US009256978B2

United States Patent
Kim et al.

(10) Patent No.: US 9,256,978 B2
(45) Date of Patent: Feb. 9, 2016

(54) IMAGE PROCESSING APPARATUS AND METHOD

(71) Applicant: SAMSUNG MEDISON CO., LTD., Gangwon-Do (KR)

(72) Inventors: Sung-yun Kim, Gangwon-Do (KR); Jun-kyo Lee, Gangwon-Do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 323 days.

(21) Appl. No.: 13/789,628

(22) Filed: Mar. 7, 2013

(65) Prior Publication Data
US 2013/0235032 A1 Sep. 12, 2013

(30) Foreign Application Priority Data

Mar. 7, 2012 (KR) .................. 10-2012-0023619

(51) Int. Cl.
*G06T 15/00* (2011.01)
*G06T 15/08* (2011.01)
*G06T 19/20* (2011.01)

(52) U.S. Cl.
CPC ................. *G06T 15/08* (2013.01); *G06T 19/20* (2013.01); *G06T 2219/2021* (2013.01)

(58) Field of Classification Search
None
See application file for complete search history.

(56) References Cited

U.S. PATENT DOCUMENTS

| 6,437,784 B1* | 8/2002 | Bentley et al. ................ 345/473 |
| 2002/0175923 A1* | 11/2002 | Lin et al. ....................... 345/629 |
| 2012/0113095 A1* | 5/2012 | Hwang et al. ................. 345/419 |

FOREIGN PATENT DOCUMENTS

JP 2011-083490 A 4/2011

OTHER PUBLICATIONS

Korean Office Action, w/ English translation thereof, issued in Korean Patent Application No. KR 10-2012-0023619 dated May 9, 2013.

* cited by examiner

*Primary Examiner* — Kee M Tung
*Assistant Examiner* — Frank Chen
(74) *Attorney, Agent, or Firm* — McDermott Will & Emery LLP

(57) ABSTRACT

An image processing apparatus and method. The image processing method includes a data obtaining unit for obtaining volume data that contains a target image; a depth-data obtaining unit for obtaining depth data that indicates a depth to the surface of the target image from an image plane; an image processing unit for processing the volume data into a processed volume data based on the depth-data, and obtaining a rendered image based on the processed volume data; and a display unit for displaying the rendered image.

18 Claims, 14 Drawing Sheets

IMAGE PROCESSING APPARATUS AND METHOD

CROSS-REFERENCE TO RELATED PATENT APPLICATION

This application claims the benefit of Korean Patent Application No. 10-2012-0023619, filed on Mar. 7, 2012, in the Korean Intellectual Property Office, the disclosure of which is incorporated herein in its entirety by reference.

BACKGROUND OF THE INVENTION

1. Field of the Invention

The present invention relates to an image processing apparatus and method.

2. Description of the Related Art

An image processing apparatus may obtain 2D rendered images with three dimensional (3D) textures by rendering volume data for stereographic images. The image processing apparatus may also process the volume data to enhance the image quality of rendered images or edit the rendered images.

Accordingly, an image processing apparatus and method is required to efficiently process the volume data.

SUMMARY OF THE INVENTION

The present invention provides an image processing apparatus and method for efficiently processing volume data.

According to an aspect of the present invention, there is provided an image processing apparatus comprising: a data obtaining unit for obtaining volume data that contains a target image; a depth-data obtaining unit for obtaining depth data that indicates a depth to the surface of the target image from an image plane: an image processing unit for processing the volume data based on the depth data into processed volume data, and obtaining a rendered image based on the processed volume data; and a display unit for displaying the rendered image.

The image processing apparatus may further comprises an input unit for receiving a edit request to edit the rendered image from a user, wherein the image processing unit obtains an edited rendered image based on the edit request and the depth-data, and the display unit displays the edited rendered image.

The image processing unit may divide the volume data into a target volume and a non-target volume on the border of the surface of the target image obtained based on the depth-data, and obtain processed volume data formed by removing the non-target volume from the volume data.

The image processing unit may obtain a mask volume that indicates the surface of the target image based on the depth-data, and mask the volume data with the mask volume to obtain the processed volume data.

The image processing unit may obtain an editing area within the rendered image based on the edit request, establish a deletion volume corresponding to the editing area in the processed volume data based on the depth-data, remove the deletion volume from the processed volume data to obtain an edited volume data, and obtain the edited rendered image based on the edited volume data.

A bottom depth of the deletion volume from the image plane may be equal to or deeper than the depth to the surface of the target image.

A top depth of the deletion volume from the image plane may be equal to or shallower than a minimum depth to the surface of the target image within the editing area, and the bottom depth of the deletion volume from the image plane may be equal to or shallower than a maximum depth to the surface of the target image within the editing area.

The edit request may further include user depth information that indicates the bottom depth of the deletion volume.

The input unit may receive a recover request to recover the edited rendered image, the image processing unit may recover the edited rendered image based on the recover request to obtain a recovered rendered image, and the display unit may display the recovered rendered image.

The image processing unit may set up the deletion volume or a part of the deletion volume from the edited volume data as a recover volume, obtain recovered volume data by recovering the recover volume in the edited volume data, and obtain the recovered rendered image based on the recovered volume data.

According to another aspect of the present invention, there is provided an image processing method comprising: obtaining volume data that contains a target image; obtaining depth data that indicates a depth to the surface of the target image from an image plane; processing the volume data based on the depth data into processed volume data, and obtaining a rendered image based on the processed volume data; and displaying the rendered image.

The image processing method may further comprises receiving an edit request to edit the rendered image from a user; obtaining an edited rendered image based on the edit request and the depth-data; and displaying the edited rendered image.

The obtaining of the processed volume data may further comprise dividing the volume data into a target volume and a non-target volume on the border of the surface of the target image obtained based on the depth-data, and removing the non-target volume from the volume data.

The obtaining of the edited rendered image may comprise obtaining an editing area within the rendered image based on the edit request, establishing a deletion volume corresponding to the editing area in the processed volume data based on the depth-data, removing the deletion volume from the processed volume data to obtain an edited volume data, and obtaining the edited rendered image based on the edited volume data.

A bottom depth of the deletion volume from the image plane may be equal to or deeper than the depth to the surface of the target image.

A top depth of the deletion volume from the image plane may be equal to or shallower than a minimum depth to the surface of the target image within the editing area, and the bottom depth of the deletion volume from the image plane may be equal to or shallower than a maximum depth to the surface of the target image within the editing area.

The edit request may further include user depth information that indicates the bottom depth of the deletion volume.

The image processing method may further comprises receiving a recover request to recover the edited rendered image, recovering the edited rendered image based on the recover request to obtain a recovered rendered image, and displaying the recovered rendered image.

The obtaining of the recovered rendered image may comprise setting up the deletion volume or a part of the deletion volume from the edited volume data as a recover volume, obtaining recovered volume data by recovering the recover volume in the edited volume data, and obtaining the recovered rendered image based on the recovered volume data.

According to another aspect of the present invention, there is provided a computer readable recording medium having embodied thereon programs that perform, when executed by a computer, the method as described above.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
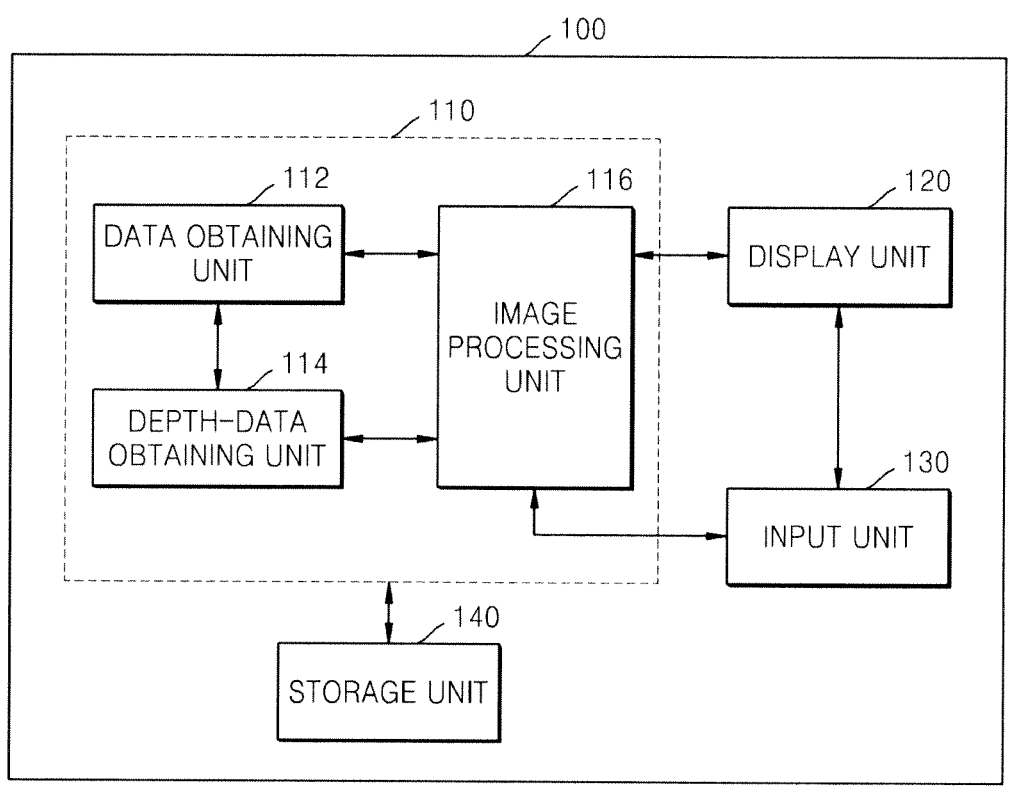
FIG. 1 is a block diagram of an image processing apparatus according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a block diagram of an image processing apparatus 100 according to an embodiment of the present invention.

Referring to FIG. 1, the image processing apparatus 100 includes a control unit 110 and a display unit 120. The image processing apparatus 100 may further include an input unit 130 and a storage unit 140.

The image processing apparatus 100 may be applied to a medical image device, such as, an ultrasound imaging device, a computed tomography (CT) device or a magnetic resonance imaging (MRI) device. For example, the image processing apparatus 100 may be incorporated in the medical imaging device. The image processing apparatus 100 may be applied not only to medical imaging devices but also to various imaging devices that require volume data to be processed.

The control unit 110 may obtain and process data to create a display image to be displayed on the display unit 120. The display unit 120 may display the display image in real time according to control by the control unit 110. The input unit 130 may receive a user request from a user. The control unit 110 may process the data based on the user request. The input unit 130 or a part of the input unit 130 may be displayed on the display unit 120.

The control unit 110 may include a data obtaining unit 112, a depth-data obtaining unit 114 and an image processing unit 116. The data obtaining unit 112 obtains volume data that contains a target image. The depth-data obtaining unit 114 obtains depth data that indicates a depth to the surface of the target image with respect to an image plane. The image processing unit 116 obtains processed volume data by processing the volume data based on the depth data, and obtains a rendered image based on the processed volume data. The display unit 120 displays the rendered image.

Figure 2:
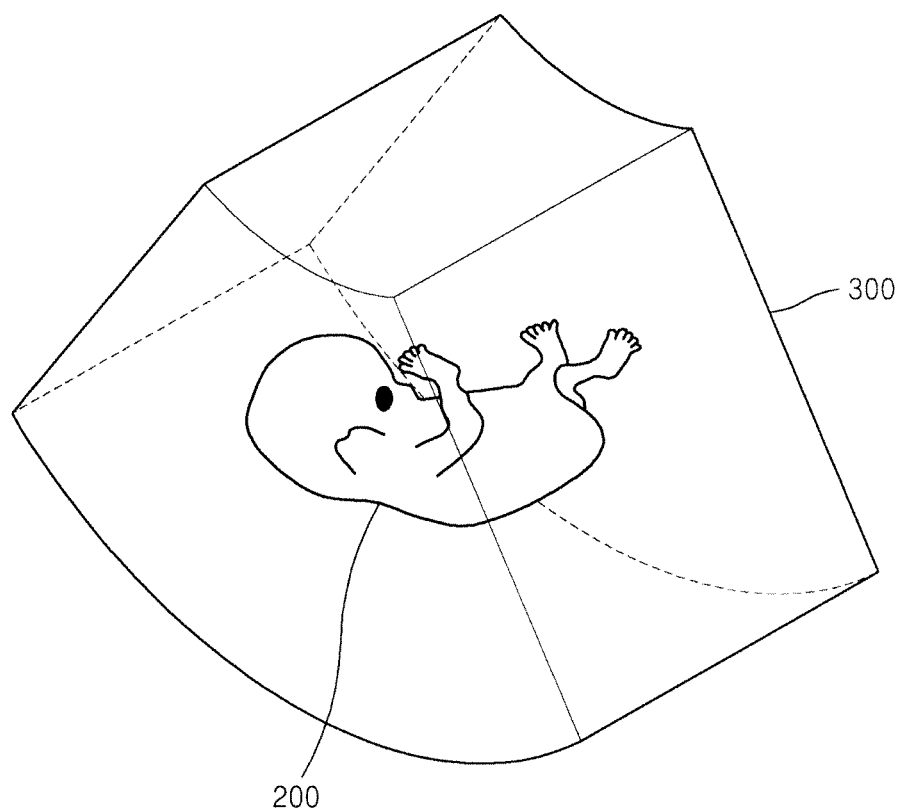
FIG. 2 depicts an example of volume data obtained by a data obtaining unit of FIG. 1.

FIG. 2 depicts an example of the volume data obtained by the data obtaining unit 112 of FIG. 1.

Referring to FIGS. 1 and 2, a volume data 300 obtained in the data obtaining unit 112 contains a target image 200. The volume data 300 may include a plurality of voxel values. The target image 200 is a stereoscopic data of a target. In FIG. 2, the target image 200 is only by way of an example the stereoscopic data of a fetus but is not limited thereto. The target may be any animal body including a human body, or a part of an animal body. For example, the target may be a fetus or an organ of an animal body.

As an example, the data obtaining unit 112 may scan a three dimensional (3D) space having a target, and may obtain the volume data 300 that may image the scanned 3D space with a 3D effect. As another example, the data obtaining unit 112 may receive scan information of the scanned target from an external scanning device, and may obtain the volume data 300 based on the scan information. As a further example, the data obtaining unit 112 may receive the volume data 300 from the external device. However, the method of obtaining the volume data in the image processing apparatus 100 is not limited thereto, but the volume data may be obtained in different ways.

Figure 3:
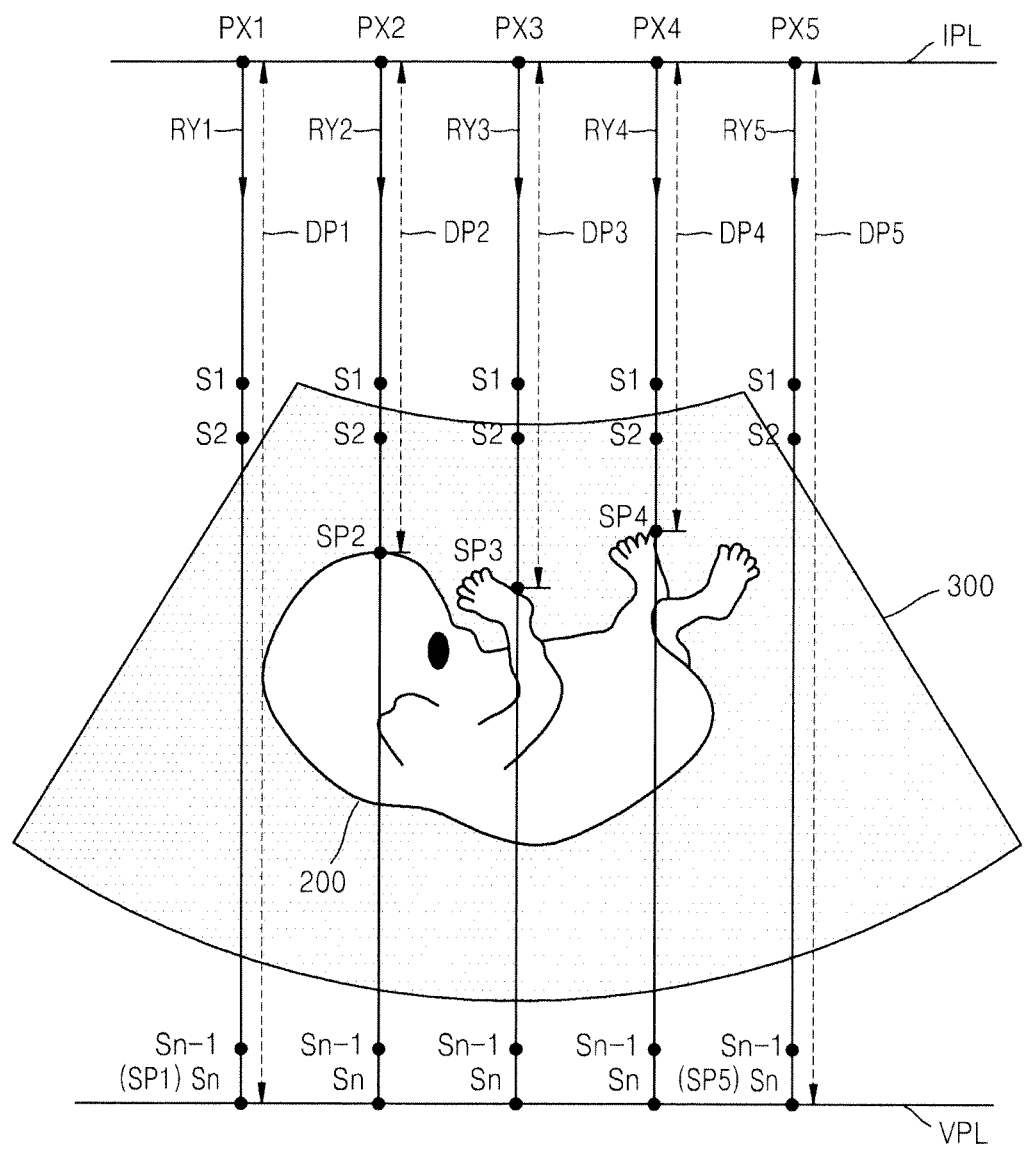
FIG. 3 depicts an example of a method of obtaining depth data performed by a depth-data obtaining unit of FIG. 1.

FIG. 3 depicts an example of a method of obtaining depth data performed by a depth-data obtaining unit 114 of FIG. 1.

Referring to FIGS. 1 and 3, the depth-data obtaining unit 114 obtains the depth data that indicates surface depths DP1-DP5 between the surface of the target image 200 and an image plane IPL.

The image plane IPL may be a virtual plane on which a viewpoint image of the volume data 300 captured by a virtual camera is formed. The viewpoint image formed on the image plane IPL may be displayed through the display unit 120.

The depth-data obtaining unit 140 may set a position and an orientation of the image plane IPL with respect to the volume data 300 in different ways. The position and the orientation of the image plane IPL may be altered based on the user request input through the input unit 130.

The image plane IPL may include a plurality of pixels PX1-PX5, which are arranged in a matrix form. FIG. 3 depicts, by way of an example, first to fifth pixels PX1-PX5 arranged in a line, but the number of the pixels to be included in the image plane IPL is not limited thereto.

The depth-data obtaining unit 114 may obtain a depth to the surface of the target image 200 for each of the plurality of pixels PX1-PX5. Accordingly, the depth data may include a plurality of depths DP1-DP5 for the plurality of pixels PX1-PX5 in the image plane IPL.

The depth-data obtaining unit 114 may obtain the depth data based on the amount of reflection of light incident to the volume data 300 from the image plane IPL. This is because the surface of the target image 200 in the volume data has more light reflection compared with parts other than the surface. Thus, the depth-data obtaining unit 114 may detect max points where the amount of reflected light is maximum in the volume data 300, and consider the max points as surface points SP1-SP5 of the target image 200. Each surface point SP1-SP5 may be a voxel. Furthermore, the depth-data obtaining unit 114 may obtain depth data based on the surface points SP1-SP5.

For example, the depth-data obtaining unit 114 may obtain the depth-data of a target image 200 based on ray casting that is used for volume rendering.

At each of the plurality of pixels PX1-PX5 in the image plane IPL, a light ray RY1-RY5 may reach a virtual plane VPL passing through the volume data 300 from the image plane IPL.

A plurality of sample points (S1, S2, . . . , Sn, where n is an integer) are established for each of the plurality of rays RY1-RY5. Each of the plurality of sample points S1, S2, . . . , Sn may be a voxel. The sample points shown in FIG. 3 are merely illustrative, and the locations of the sample points, gaps between the sample points, the number of the sample points, etc. are not limited thereto.

With ray casting, the light reflection is obtained at each of the plurality of sample points S1, S2, . . . , Sn on one of the plurality of rays RY1-RY5, and thus a total sum of the reflections for the ray is obtained by summing all the reflections at the plurality of sample points on the ray. For example, a total sum TS(2) of the reflections at sample points S1, S2, . . . , Sn on a second ray RY2 may be obtained as given by equation (1):

$$TS(2) = \sum_{i}^{n} Di \prod_{j}^{i-1} Tj$$  ⟨Equation 1⟩ where Di is an intensity of light at an $i^{th}$ sample point Si of the second ray RY2, and Tj is transparency at a $j^{th}$ sample point Sj of the second ray RY2.

The depth-data obtaining unit 114 may detect a max reflection among the plurality of sample points S1, S1, . . . , Sn of each of the plurality of rays RY1-RY5, and presume the max reflection to be a surface point SP1-SP5 of the target image 200. For example, the depth-data obtaining unit 114 may detect the max reflection Tmax(2) among the sample points S1, S2, . . . , Sn of the second ray RY2 as in equation (2):

$$T\max(2) = \max_{i} \left\{ Di \prod_{j}^{i-1} Tj \right\}$$  ⟨Equation 2⟩

The depth-data obtaining unit 114 may detect the max reflection Tmax(2) among the sample points S1, S1, . . . , Sn of the second ray RY2 as the second surface point SP2.

The depth-data obtaining unit 114 may presume the second surface point SP2 of the second ray RY2 to be in the surface of the target image 200 with respect to the second pixel PX2, and obtain the depth between the second surface point SP2 and the second pixel PX2 as a second surface depth DP2. The depth-data obtaining unit 114 may also obtain depth data for the remaining rays by obtaining their depths to the surface.

The image processing unit 116 will now be described.

The image processing unit 116 obtains processed volume data by processing the volume data 300 based on the depth data. The image processing unit 116 may divide the volume data 300 into a target volume and a non-target volume on the border of the surface of the target image 200 obtained based on the depth data. The image processing unit 116 may obtain the processed volume data with the non-target volume removed from the volume data 300.

Figure 4:
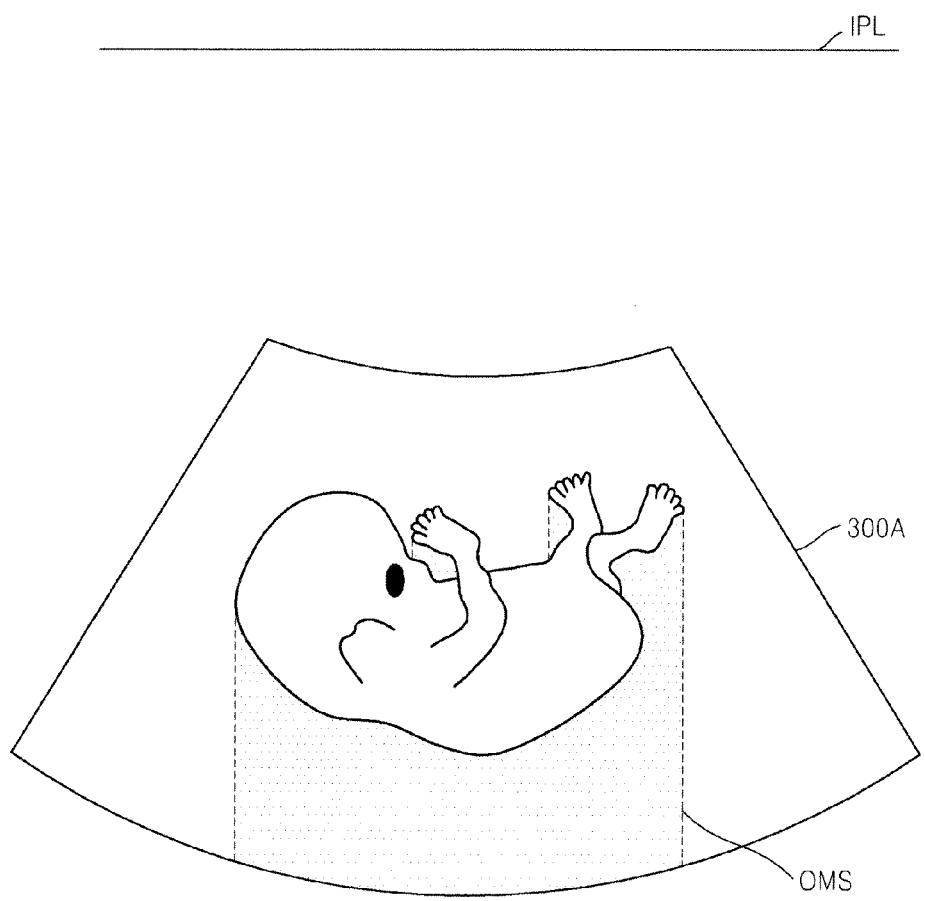
FIG. 4 depicts an example of processed volume data obtained by an image processing unit of FIG. 1.

FIG. 4 depicts an example of the processed volume data obtained by the image processing unit 116 of FIG. 1. It is assumed that the processed volume data 300A shown in FIG. 4 is obtained by the image processing unit 116 of FIG. 1 by processing the volume data 300 of FIG. 3 based on the depth data.

Referring to FIGS. 3 and 4, the processed volume data 300A may result from eliminating the non-target volume from the volume data 300 with respect to the surface of the target image 200 (OMS). The non-target volume may have a depth with respect to the image plane IPL less than the depth to the surface of the target image 200 (OMS). Removal of the non-target volume may refer to altering each value of the plurality of voxels included in the non-target volume from among the values of the plurality of voxels included in the volume data 300 to a reference value. Voxels whose values are altered to the reference value may be presented in a reference color, such as, in a black.

As such, the image processing unit 116 of FIG. 1 may only remove the non-target volume from the volume data 300 while maintaining the surface of the target image 200 OMS and a volume deeper than the OMS. The non-target volume is likely to be noise or an obstacle to which the depth is shallower than the depth to the surface of the target image 200 (OMS). Thus, the image processing unit 116 of FIG. 1 may remove the noise or obstacle from the volume data 300 while preserving the surface of the target image 200 (OMS).

Figure 5:
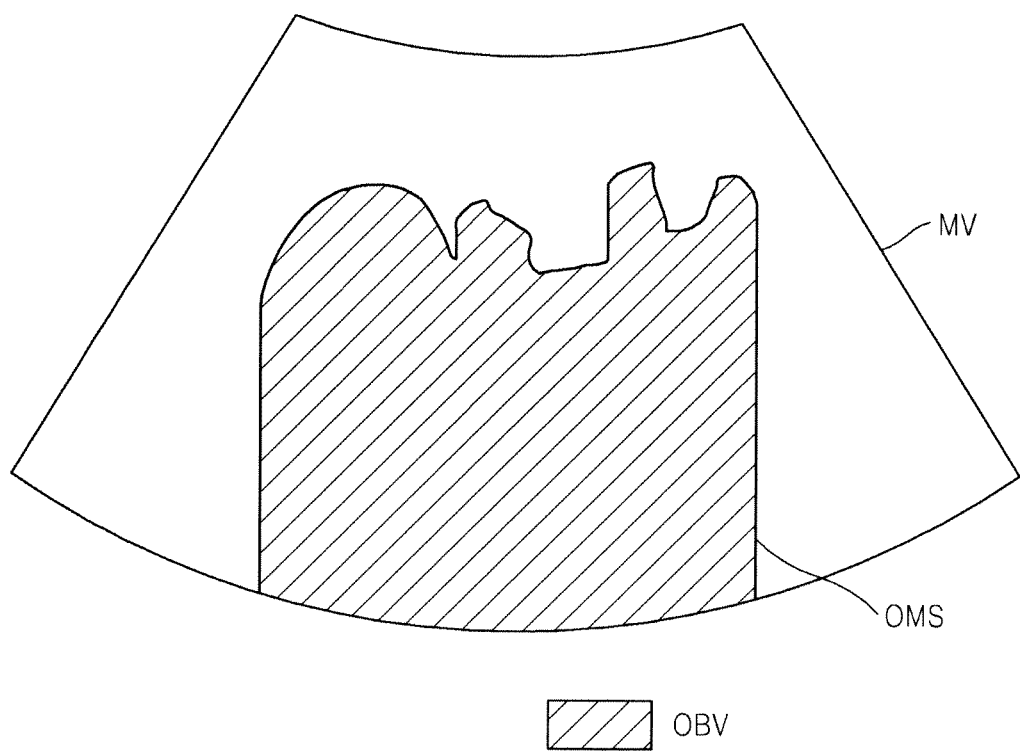
FIG. 5 depicts an example of a mask volume used by the image processing unit of FIG. 1 to obtain the processed volume data.

FIG. 5 depicts an example of a mask volume used by the image processing unit 116 of FIG. 1 to obtain the processed volume data.

Referring to FIG. 5, the image processing unit 116 of FIG. 1 may obtain the mask volume that indicates the surface of the target image (OMS) based on the depth data. A hatched part of the mask volume MV may indicate the target volume OBV while a non-hatched part indicates the non-target volume.

Turning back to FIGS. 3 to 5, the image processing unit 116 of FIG. 1 may obtain the processed volume data by masking the volume data 300 with the mask volume MV. Masking may be an image processing operation which involves matching the volume data 300 and the mask volume MV, and removing the non-target volume (non-hatched part) indicated by the mask volume MV from the volume data 300 to obtain the processed volume data 300A.

The image processing unit 116 obtains a rendered image based on the processed volume data 300A. The rendered image may be a viewpoint image of the processed volume data 300A, which is formed on the image plane IPL. The image processing unit 116 may obtain the rendered image based on the ray casting. However, the image processing unit 116 may obtain the rendered image based not only on the ray casting but also on various volume rendering methods. The display unit 120 of FIG. 1 displays the rendered image.

Figure 6:
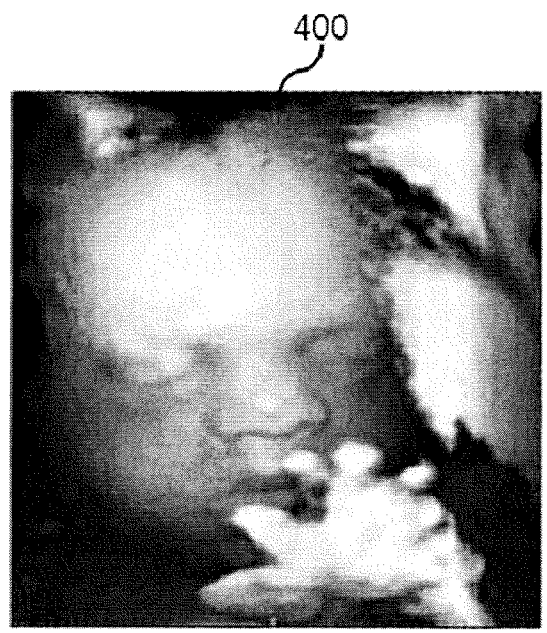
FIG. 6 shows an example of a rendered image where a target is a fetus.

FIG. 6 shows an example of the rendered image where the target is a fetus.

Referring to FIGS. 1 and 6, parts of the face of the target appears hidden by the hand of the target in the rendering image 400. In connection with FIG. 3, this is because the depth to the hand of the target image 200 from the image plane IPL is shallower than the depth to the face of the target image 200.

In this regard, only the face of the target may be a region of interest. The hand of the target may be a region of non-interest. Thus, when the rendered image 400 includes the region of non-interest, a method of editing the rendered image 400 by eliminating the region of non-interest from the rendered image 400 is required.

The input unit 130 may receive an edit request to edit the rendered image 400 from a user. The image processing unit 116 may obtain an edited rendered image based on the edit request received through the input unit 130 and the depth data obtained by the depth-data obtaining unit 114. The display unit 120 may display the edited rendered image.

Figure 7:
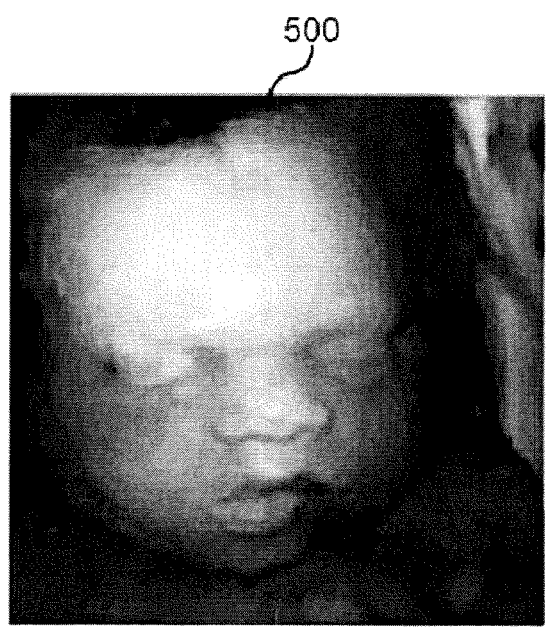
FIG. 7 shows another example of an edited rendered image where the target is the fetus.

FIG. 7 shows another example of the edited rendered image where the target is the fetus. Assuming that the edited rendered image 500 of FIG. 7 is obtained from the rendered image 400 based on the edit request and the depth data.

Referring to FIGS. 6 and 7, the hand in the edited rendered image 500, which is the region of non-interest displayed in the rendered image 400, is removed. Again, the edited rendered image 500 has the face of the target which was hidden by the hand of the target being viewed.

Next, an example of a method of obtaining the edited rendered image 500 from the rendered image 400 in the image processing unit 116 will be described.

The image processing unit 116 may obtain an editing area based on the edit request, establish a deletion volume, which corresponds to the editing area, in the processed volume data based on the depth data, obtain an edited volume data having the deletion volume eliminated from the processed volume data, and obtain the edited rendered image based on the edited volume data.

Figure 8:
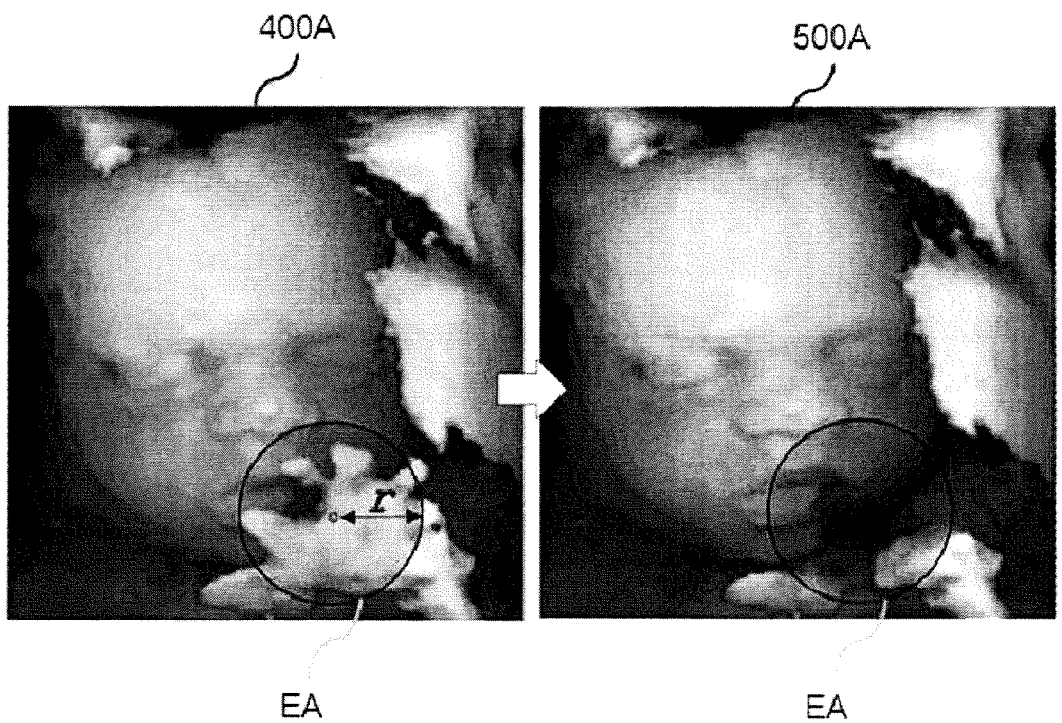
FIG. 8 shows examples of the rendered image in which an editing area is set up and the edited rendered image.

FIG. 8 shows examples of the rendered image having an editing area set up, and the edited rendered image;

Referring to FIGS. 1 and 8, the image processing unit 116 may set up the editing area EA in the rendered image 400A based on the edit request received through the input unit 130. The display unit 120 may display the rendered image 400A in which the editing area EA is set up. The display unit 120 may also display the edited rendered image 500A formed by editing the rendered image 400A in the editing area EA. The editing area EA is illustrated in a circle, but is not limited thereto.

The edit request may include editing area information that indicates the editing area EA.

As an example, the user may input the editing area information by directly selecting the editing area EA on the displayed rendered image 400A. For example, the user may select the editing area EA on the rendered image 400A through the input unit 130 that can be implemented with a mouse, a track ball, etc.

As another example, the user may input the editing area information by selecting a point on the rendered image 400A displayed on the display unit 130. The image processing unit 116 may set up the editing area EA based on the point. For example, a circle centered on the point may be set up as the editing area EA. The radius r of the editing area EA may be predetermined by default or adjusted by the user. Alternatively, an oval or a square with respect to the point may be set up as the editing area EA.

The image processing unit 116 may set up a deletion volume, which corresponds to the editing area EA established on the rendered image 400A, within the processed volume data.

Figure 9:
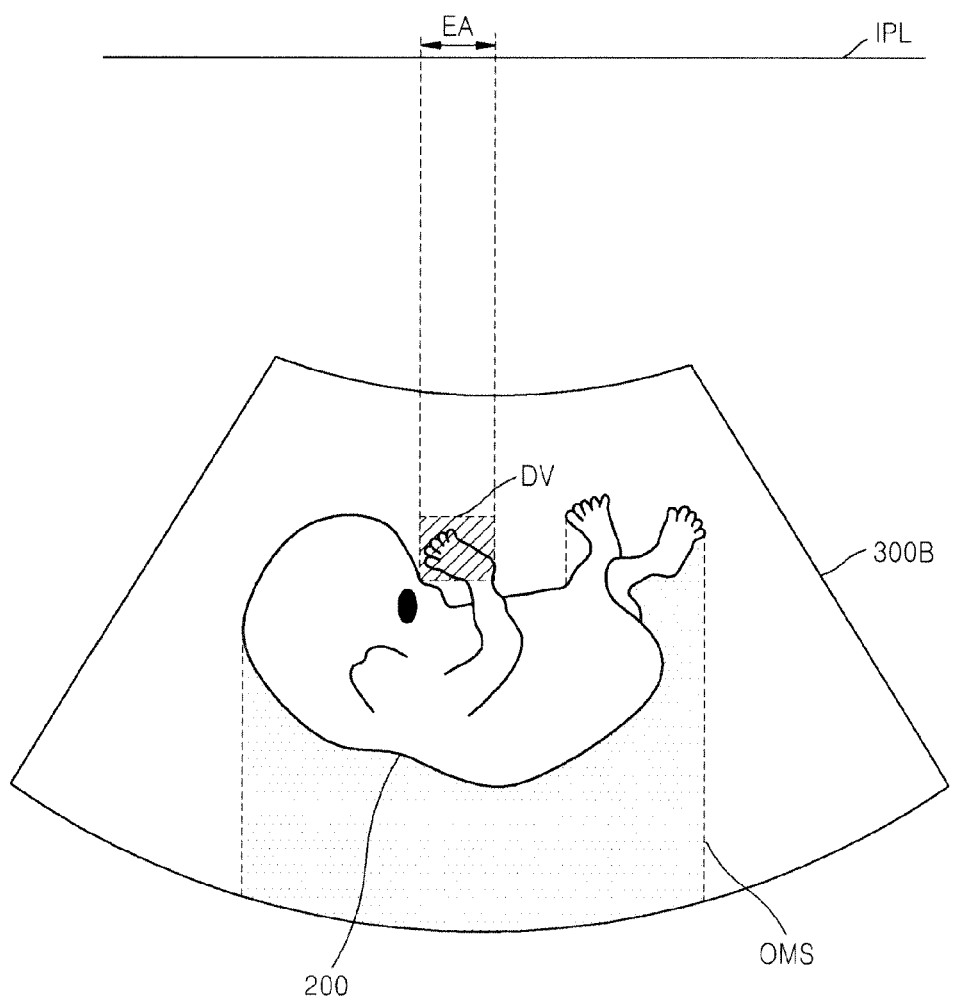
FIG. 9 depicts an example of the processed volume data in which a deletion volume is set up.
Figure 10:
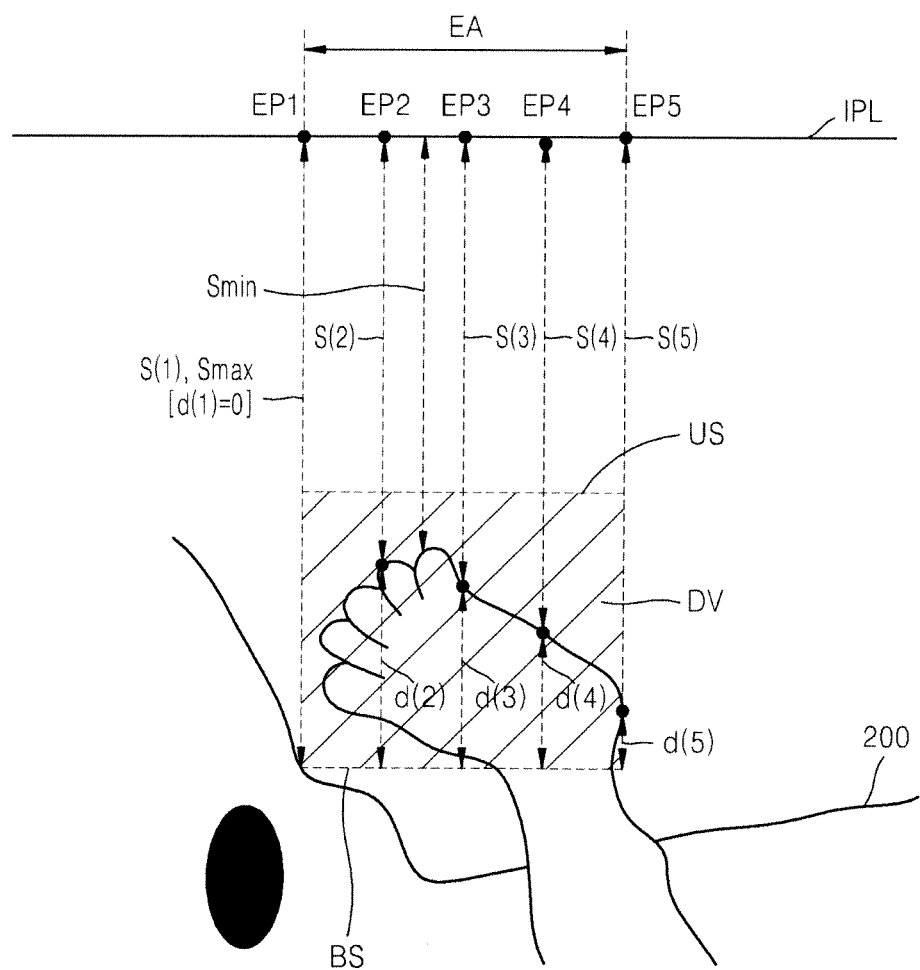
FIG. 10 shows an enlargement of a part of FIG. 9.
Figure 11:
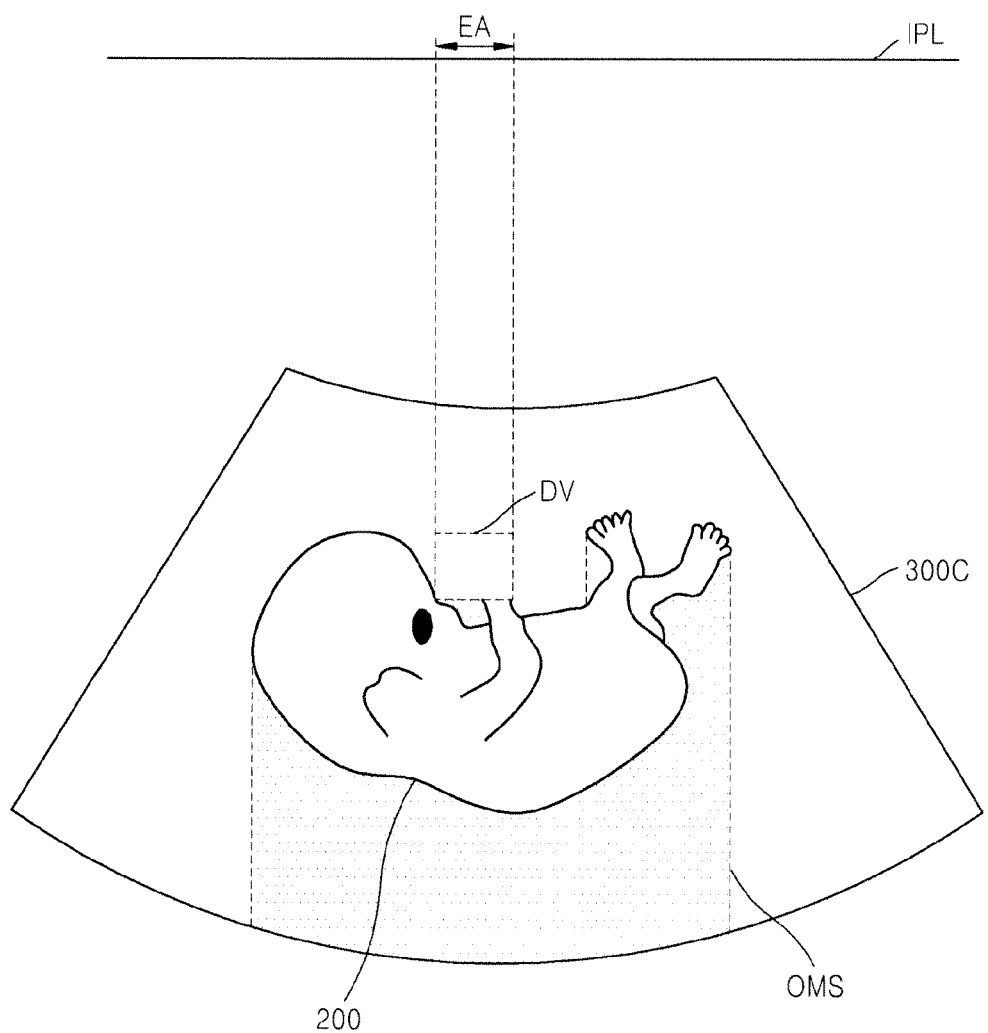
FIG. 11 depicts an example of an edited volume data obtained by removing the deletion volume from the processed volume data.

FIG. 9 depicts an example of the processed volume data in which the deletion volume is set up, FIG. 10 shows an enlargement of a part of FIG. 9, and FIG. 11 depicts an example of edited volume data obtained by removing the deletion volume from the processed volume data.

Referring to FIGS. 1 and 9 to 11, the image processing unit 116 may set up the deletion volume DV, which corresponds to the editing area EA, within the processed volume data 300B based on the editing area EA in the image plane IPL, and then obtain the edited volume data 300C by removing the deletion volume DV from the processed volume data 300B.

The editing area EA in the image plane IPL may include at least one pixel (EP1-EP5). Although the first to fifth pixels (EP1-EP5) are shown in a row in FIG. 10, they are merely illustrative and the number of the at least one pixel included in the editing area EA is not limited. The pixels (EP1-EP5) of FIG. 10 may be ones, which are included in the editing area EA, from among the pixels (PX1-PX5).

A depth from the image plane IPL to a bottom surface BS of the deletion volume DV may be equal to or deeper than the depth to the corresponding surface [S(p), p=1, 2, ..., 5] of the target image 200. That is, the depth from the image plane IPL to the bottom surface BS of the deletion volume DV may be deeper than the depth to the corresponding surface [S(p), p=1, 2, ..., 5] of the target image 200 by a corresponding deletion depth [d(p), p=1, 2, ..., 5].

In FIG. 10, the depth to the bottom surface BS of the deletion volume DV from the first pixel EP1 is equal to the depth to the surface S(1) of the target image 200. That is, the first deletion depth d(1) is 0. Furthermore, the depth to the bottom surface BS of the deletion volume DV from the third pixel EP3 is deeper than the depth to the surface S(3) of the target image 200 by the third deletion depth d(3).

The deletion depth d(p) may be set up in different ways. The deletion depth d(p) may be set up constantly or differently for the plurality of pixels EP1-EP5 included in the editing area EA.

The deletion depth d(p) may have an automatically established value. The deletion depth d(p) for the pth pixel EPp (p=1, 2, ..., 5), one of the at least one pixels EP1-EP5 in the editing area EA, may be set up based on at least one of the following: the position of the pth pixel EPp within the editing area EA, the depth to the surface S(p) of the target image 200 for the pth pixel EPp, and the maximum depth to the surface Smax of the target image 200 within the editing area EA.

The shallower the depth to the surface S(p) of the target image 200 for the pth pixel EPp is, the thicker the deletion depth d(p) becomes. Furthermore, the deeper the depth to the surface S(p) of the target image 200 for the pth pixel EPp is, the thinner the deletion depth d(p) becomes.

In addition, the depth to the upper surface (US) of the deletion volume from the image plane IPL may be equal to or shallower than the minimum depth to the surface Smin of the target image 200 within the editing area EA. Furthermore, the depth to the bottom surface BS of the deletion volume DV from the image plane IPL may be equal to or shallower than the maximum depth to the surface Smax of the target image 200 within the editing area EA.

For example, the deletion depth d(p) for the corresponding pth pixel EPp may be obtained by the following equation:

$$d(p) = e^{-\frac{|p-c|^2}{2r^2}} (S\max - S(p)) \qquad \langle \text{Equation 3} \rangle$$

where p represents the position of the pth pixel PXp in the editing area EA, c represents a center point of the editing area EA, and r represents the radius of the editing area EA.

Alternatively, the deletion depth d(p) may have a value that is adjusted by the user. To adjust the deletion depth d(p), the edit request may further include user depth information that indicates the depth to the bottom surface BS of the deletion volume DV. The edit request may further include user depth information that indicates the deletion depth d(p).

As such, the image processing unit 116 may obtain the edited volume data 300C, and obtain the edited rendered image (e.g., the rendered image 500A of FIG. 8) based on the edited volume data 300C.

When the edited rendered image also includes a region of non-interest, the user may re-input an edit request to re-edit the edited rendered image. The method of re-editing the edited rendered image may employ the method of editing the rendered image (e.g., 400A). Herein, any overlapping description will be omitted.

The aim of the edited rendered image is to have the region of non-interest removed from the rendered image, but in the editing process not only the region of non-interest but also the region of interest may be removed. In addition, in the editing process, the region of non-interest may be changed into the region of interest. Accordingly, a method of recovering a part or all of the removed region of non-interest from the edited rendered image is required.

Returning to FIG. 1, the input unit 130 may receive a recover request for recovering the edited rendered image (e.g. the rendered image 500A of FIG. 8). The image processing unit 116 may obtain a recovered rendered image based on the recover request. The display unit 120 may display the recovered rendered image.

Figure 12:
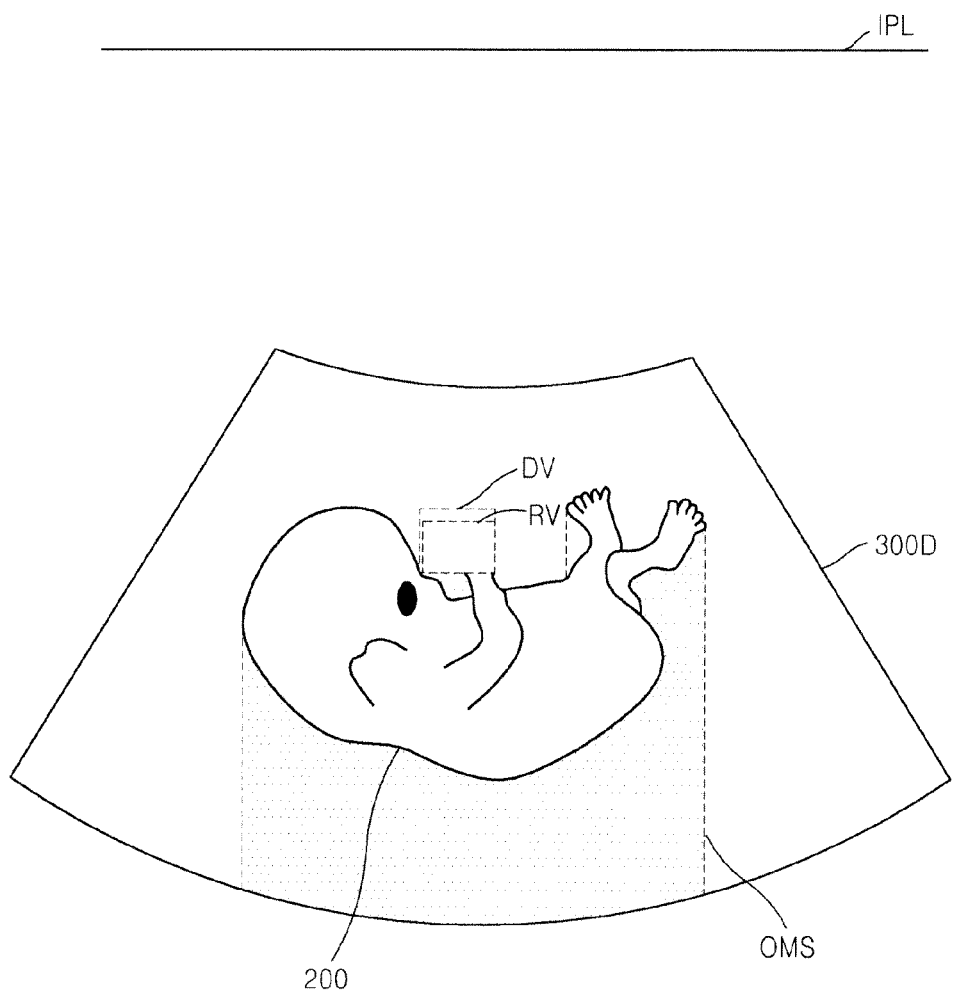
FIG. 12 depicts an example of the edited volume data for the edited rendered image.
Figure 13:
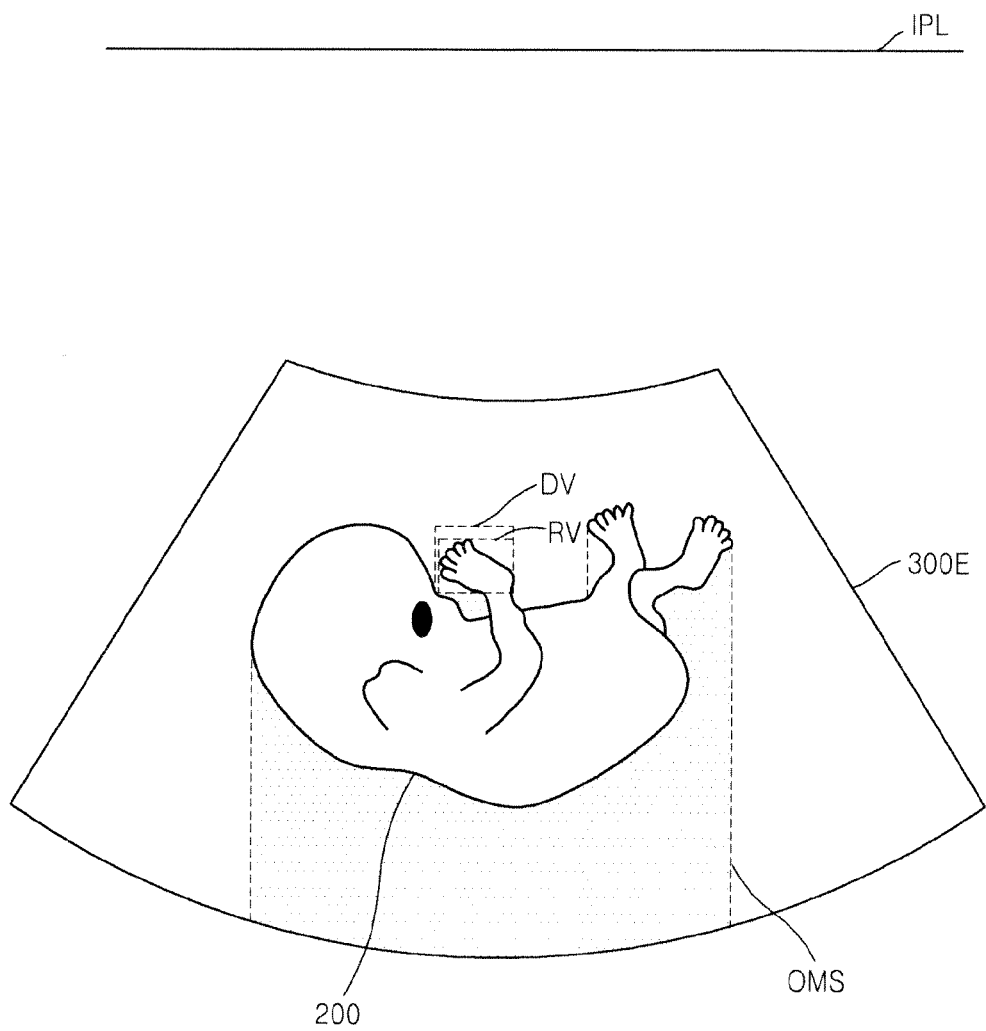
FIG. 13 depicts an example of recovered volume data for a recovered rendered image.

FIG. 12 depicts an example of the edited volume data for the edited rendered image, and FIG. 13 depicts an example of recovered volume data for a recovered rendered image.

Referring to FIGS. 1, 12 and 13, the image processing unit 116 may set up a recover volume RV in the edited volume data 300D. The recover volume RV may be the deletion volume DV or a part of the deletion volume DV. The bottom surface of the recover volume RV may be consistent with the bottom surface of the deletion volume DV.

The image processing unit 116 may obtain recovered volume data 300E by recovering the recover volume RV in the edited volume data 300D.

The storage unit 140 may store volume data, processed volume data, edited volume data, recovered volume data, etc., which are processed by the control unit 110. The image processing unit 116 may recover the recover volume RV based on the processed volume data stored in the storage unit 140.

Figure 14:
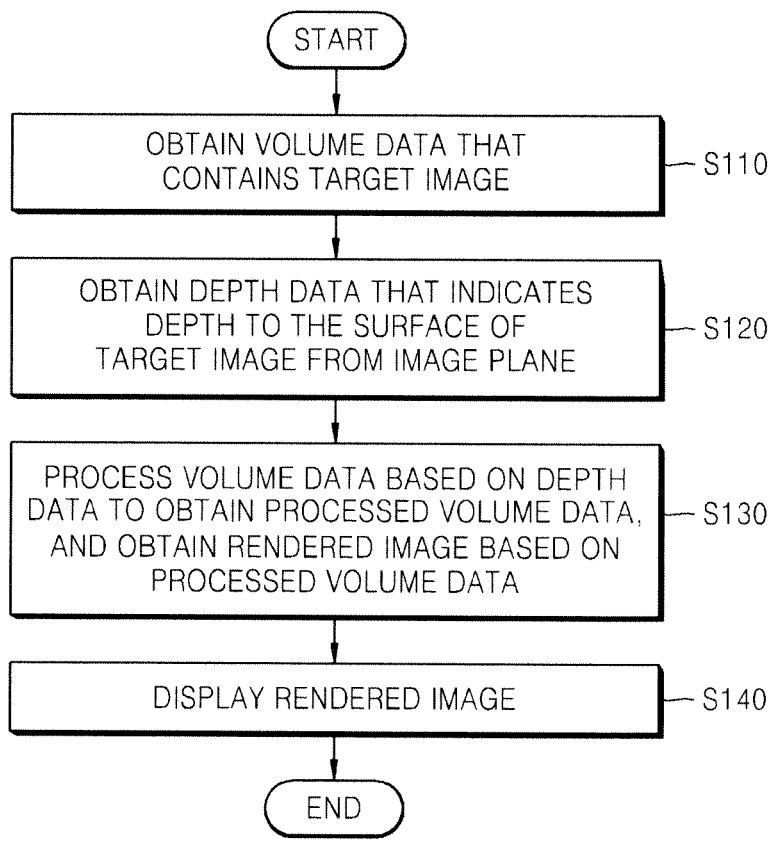
FIG. 14 is a flowchart of an image processing method according to an embodiment of the present invention.

FIG. 14 is a flowchart of the image processing method according to an embodiment of the present invention.

Referring to FIG. 14, initially, volume data containing a target image is obtained in operation S110. Depth data indicating a depth to the surface of the target image from an image plane IPL is obtained, in operation S120. Processed volume data is obtained by processing the volume data based on the depth data, and a rendered image is obtained based on the processed volume data, in operation S130. The rendered image is displayed in operation S140.

The image processing method shown in FIG. 14 may be performed by the image processing apparatus shown in FIG. 1. Each step of the image processing method employs the steps described in connection with FIGS. 1 to 13. Herein, any overlapping description will be omitted.

Figure 15:
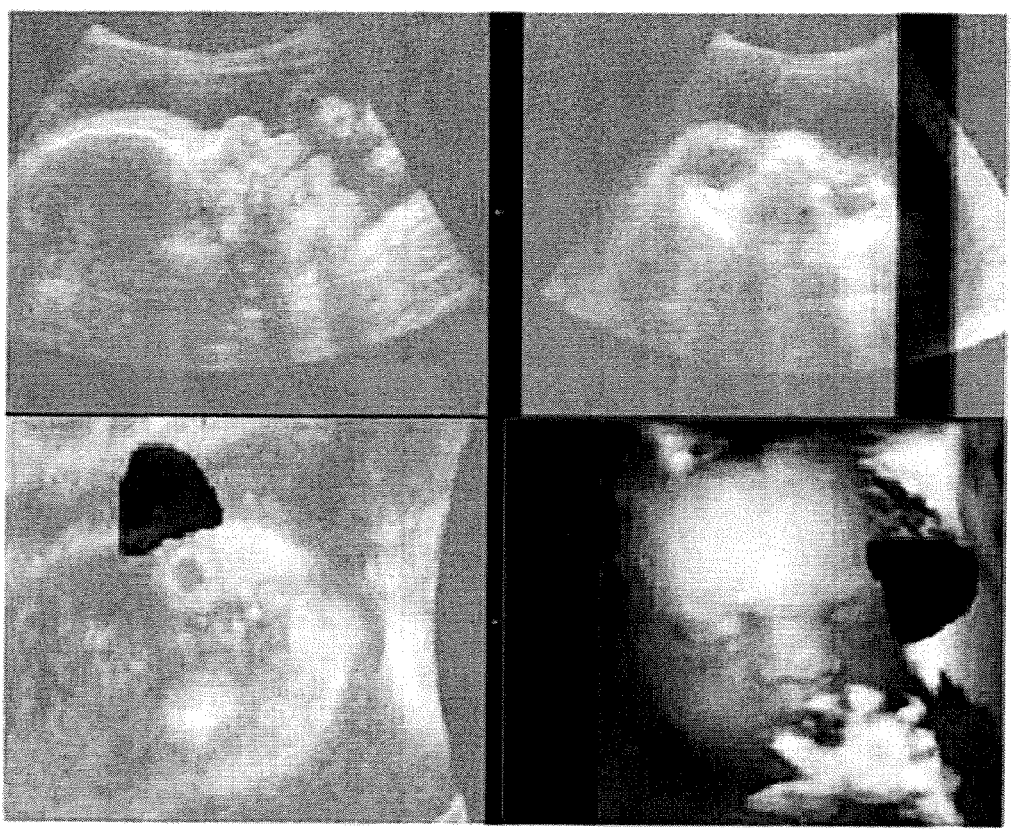
FIG. 15 shows an example of the edited rendered image obtained by performing an image processing method different from the embodiments of the present invention.

FIG. 15 shows an example of the edited rendered image obtained by performing different image processing method from the embodiments of the present invention.

Referring to FIG. 15, a specific area may be removed from the volume data using a magic-cut functionality, and the rendered image may be obtained based on the volume data having the specific area removed. Meanwhile, in FIG. 15, the edited rendered image shows discontinuity between the removed area and its surroundings, thus appearing unnatural and artificial. In addition, even an area whose removal was not desired may be removed from the volume data.

On the other hand, referring to FIG. 8, the edited rendered image 500A according to an embodiment of the present invention shows continuity between the editing area EA and its surroundings, thus appearing natural and non-artificial.

As such, according to the embodiments of the present invention, the image processing apparatus and method may be provided to efficiently process the volume data.

According to the embodiments of the present invention, the non-target volume may selectively be removed from the volume data. The non-target volume is likely to be noise or an obstacle to which the depth is shallower than the depth to the surface of the target image. Thus, the quality of the rendered image may be enhanced because the noise or obstacle could be removed from the volume data while preserving the surface of the target image.

Furthermore, according to the embodiment of the present invention, by processing the volume data based on the depth data, the edited rendered image may be obtained in which a region of interest is disclosed while removing the region of non-interest that hides the region of interest. In addition, once the user sets up the editing area through the edit request, the edited rendered image may then be obtained. In conclusion, a more intuitive and convenient-to-use method of editing a rendered image may be provided for the user.

The foregoing method may be written as computer programs and may be implemented in general-use digital computers that execute the programs using a computer readable recording medium. The data structure used in the method can be recorded on the computer readable recording medium by means of various means. Examples of the computer readable recording medium include magnetic storage media (e.g., read only memory (ROM), random access memory (RAM), universal serial bus (USB), floppy disk, hard disk, etc.), and optical recording media (e.g., CD-ROM, or DVD).

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An image processing apparatus comprising:
   a data obtaining unit configured to obtain volume data that contains a target image, the volume data including voxels;
   a depth-data obtaining unit configured to detect a surface of the target image based on the amount of reflection of light incident to the voxels included in the volume data and obtain depth data that indicates a depth to the surface of the target image from an image plane;
   an image processor configured to divide the volume data into a target volume and a non-target volume on the border of the surface of the target image obtained based on the depth-data, obtain processed volume data formed by removing the non-target volume from the volume data, and obtain a rendered image based on the processed volume data; and
   a display configured to display the rendered image, wherein the removing the non-target volume from the volume data includes altering each value of the plurality of voxels included in the non-target volume to a reference value.

2. The image processing apparatus of claim 1, further comprising
an input unit configured to receive an edit request to edit the rendered image from a user,
wherein the image processor obtains an edited rendered image based on the edit request and the depth-data, and the display displays the edited rendered image.

3. The image processing apparatus of claim 2, wherein the image processor
obtains an editing area within the rendered image based on the edit request, establishes a deletion volume corresponding to the editing area in the processed volume data based on the depth-data, removes the deletion volume from the processed volume data to obtain an edited volume data, and obtains the edited rendered image based on the edited volume data.

4. The image processing apparatus of claim 3,
wherein a bottom depth of the deletion volume from the image plane is equal to or deeper than the depth to the surface of the target image.

5. The image processing apparatus of claim 4,
wherein a top depth of the deletion volume from the image plane is equal to or shallower than a minimum depth to the surface of the target image within the editing area, and
wherein the bottom depth of the deletion volume from the image plane is equal to or shallower than a maximum depth to the surface of the target image within the editing area.

6. The image processing apparatus of claim 5,
wherein the edit request further includes user depth information that indicates the bottom depth of the deletion volume.

7. The image processing apparatus of claim 5,
wherein the input unit receives a recover request to recover the edited rendered image,
wherein the image processor recovers the edited rendered image based on the recover request to obtain a recovered rendered image,
and wherein the display displays the recovered rendered image.

8. The image processing apparatus of claim 7, wherein the image processor sets up the deletion volume or a part of the deletion volume from the edited volume data as a recover volume, obtains recovered volume data by recovering the recover volume in the edited volume data, and obtains the recovered rendered image based on the recovered volume data.

9. The image processing apparatus of claim 1, wherein the image processor
obtains a mask volume that indicates the surface of the target image based on the depth-data, and masks the volume data with the mask volume to obtain the processed volume data.

10. An image processing method comprising:
obtaining volume data that contains a target image, the volume data including voxels;
detecting a surface of the target image based on the amount of reflection of light incident to the voxels included in the volume data, and obtaining depth data that indicates a depth to the surface of the target image from an image plane;
dividing the volume data into a target volume and a non-target volume on the border of the surface of the target image obtained based on the depth-data, obtaining processed volume data formed by removing the non-target volume from the volume data, and obtaining a rendered image based on the processed volume data; and
displaying the rendered image,
wherein the removing the non-target volume from the volume data includes altering each value of the plurality of voxels included in the non-target volume to a reference value.

11. The image processing method of claim 10, further comprising
receiving an edit request to edit the rendered image from a user;
obtaining an edited rendered image based on the edit request and the depth-data; and
displaying the edited rendered image.

12. The image processing method of claim 11, wherein the obtaining of the edited rendered image comprises
obtaining an editing area within the rendered image based on the edit request,
establishing a deletion volume corresponding to the editing area in the processed volume data based on the depth-data,
removing the deletion volume from the processed volume data to obtain an edited volume data, and
obtaining the edited rendered image based on the edited volume data.

13. The image processing method of claim 12,
wherein a bottom depth of the deletion volume from the image plane is equal to or deeper than the depth to the surface of the target image.

14. The image processing method of claim 13,
wherein a top depth of the deletion volume from the image plane is equal to or shallower than a minimum depth to the surface of the target image within the editing area, and
wherein the bottom depth of the deletion volume from the image plane is equal to or shallower than a maximum depth to the surface of the target image within the editing area.

15. The image processing method of claim 14,
wherein the edit request further includes user depth information that indicates the bottom depth of the deletion volume.

16. The image processing method of claim 14, further comprising
receiving a recover request to recover the edited rendered image,
recovering the edited rendered image based on the recover request to obtain a recovered rendered image, and
displaying the recovered rendered image.

17. The image processing method of claim 16, wherein obtaining of the recovered rendered image comprises
setting up the deletion volume or a part of the deletion volume from the edited volume data as a recover volume,
obtaining recovered volume data by recovering the recover volume in the edited volume data, and
obtaining the recovered rendered image based on the recovered volume data.

18. A non-transitory computer readable recording medium having embodied thereon programs that perform, when executed by a computer, the method of claim 10.

* * * * *